(12) United States Patent
Buehler et al.

(10) Patent No.: US 8,681,345 B2
(45) Date of Patent: Mar. 25, 2014

(54) SYSTEM AND METHOD FOR MEASURING PHOTOVOLTAIC MODULE THICKNESS

(75) Inventors: Pat Buehler, Pemberville, OH (US); David Kahle, Monclova, OH (US)

(73) Assignee: First Solar, Inc., Perrysburg, OH (US)

( * ) Notice: Subject to any disclaimer, the term of this patent is extended or adjusted under 35 U.S.C. 154(b) by 306 days.

(21) Appl. No.: 13/072,031

(22) Filed: Mar. 25, 2011

(65) Prior Publication Data

US 2011/0235055 A1   Sep. 29, 2011

Related U.S. Application Data

(60) Provisional application No. 61/317,533, filed on Mar. 25, 2010.

(51) Int. Cl.
  *G01B 11/28* (2006.01)

(52) U.S. Cl.
  USPC .......................................................... 356/630

(58) Field of Classification Search
  USPC ...................... 356/630; 250/559.27
  See application file for complete search history.

(56) References Cited

U.S. PATENT DOCUMENTS

| | | | | |
|---|---|---|---|---|
| 3,536,405 A * | 10/1970 | Flower | ........................... | 356/631 |
| 3,565,531 A * | 2/1971 | Kane | ........................... | 356/631 |
| 3,671,726 A * | 6/1972 | Kerr | ........................... | 702/172 |
| 4,773,760 A * | 9/1988 | Makkonen | ........................... | 356/631 |
| 5,210,593 A * | 5/1993 | Kramer | ........................... | 356/631 |
| 5,581,353 A * | 12/1996 | Taylor | ........................... | 356/631 |
| 5,661,250 A * | 8/1997 | Katahira et al. | ........................... | 73/865.8 |
| 5,696,589 A * | 12/1997 | Bernacki | ........................... | 356/630 |
| 6,038,028 A * | 3/2000 | Grann et al. | ........................... | 356/630 |
| 6,100,986 A * | 8/2000 | Rydningen | ........................... | 356/630 |
| 6,281,679 B1 * | 8/2001 | King et al. | ........................... | 324/229 |
| 6,441,905 B1 * | 8/2002 | Tojyo et al. | ........................... | 356/429 |
| 6,757,069 B2 * | 6/2004 | Bowles | ........................... | 356/630 |
| 6,836,331 B2 * | 12/2004 | Reis et al. | ........................... | 356/429 |
| 6,937,350 B2 * | 8/2005 | Shirley | ........................... | 356/630 |
| 6,967,726 B2 * | 11/2005 | King et al. | ........................... | 356/630 |
| 7,280,232 B2 * | 10/2007 | Bristow et al. | ........................... | 356/630 |
| 7,283,256 B2 * | 10/2007 | Bristow et al. | ........................... | 356/630 |
| 7,880,156 B2 * | 2/2011 | Shakespeare | ........................... | 250/559.4 |
| 8,064,072 B2 * | 11/2011 | Schmitt et al. | ........................... | 356/630 |
| 2005/0073694 A1 * | 4/2005 | King et al. | ........................... | 356/630 |
| 2006/0061775 A1 * | 3/2006 | Bristow et al. | ........................... | 356/630 |
| 2006/0181715 A1 * | 8/2006 | Bristow et al. | ........................... | 356/630 |
| 2010/0073689 A1 * | 3/2010 | Schmitt et al. | ........................... | 356/630 |
| 2010/0214555 A1 * | 8/2010 | Schmitt et al. | ........................... | 356/72 |

* cited by examiner

*Primary Examiner* — Roy M Punnoose
(74) *Attorney, Agent, or Firm* — Dickstein Shapiro LLP

(57) ABSTRACT

A system for determining a thickness of a photovoltaic module may include a first displacement sensor and a second displacement sensor along a shared axis. The system may also include a support structure that supports the first and second displacement sensors and locates the sensors on either side of the photovoltaic module.

44 Claims, 7 Drawing Sheets

SYSTEM AND METHOD FOR MEASURING PHOTOVOLTAIC MODULE THICKNESS

CROSS-REFERENCE TO RELATED APPLICATIONS

This application claims the benefit of U.S. provisional application 61/317,533, filed on Mar. 25, 2010, which is incorporated herein by reference in its entirety.

TECHNICAL FIELD

The present invention relates to photovoltaic modules and methods of measuring the thickness of same.

BACKGROUND

The thickness or change in thickness across an encapsulated photovoltaic module may be used for process control and reliability prediction. A relatively large difference in thickness between two adjacent measuring points in a single module, referred to as pinch, may correlate to field failures within the module, such as cracks in the glass or within the solar cells or film of the module, burn spots, electrical short circuits, and other failures. Traditional methods of measuring module thickness, to determine if the module is pinched, involved operators taking measurements at various locations on a module using micrometers. One drawback of such methods is that the operator performing the measurement is often incapable of locating the measurement position accurately. Furthermore, the thickness measurement highly depends on the technique used (e.g., angle, force, etc.). Accordingly, the accuracy and repeatability of such methods may be quite poor. As a result, an apparatus and method is needed to more accurately measure the thickness of PV modules.

DETAILED DESCRIPTION

Figure 1:
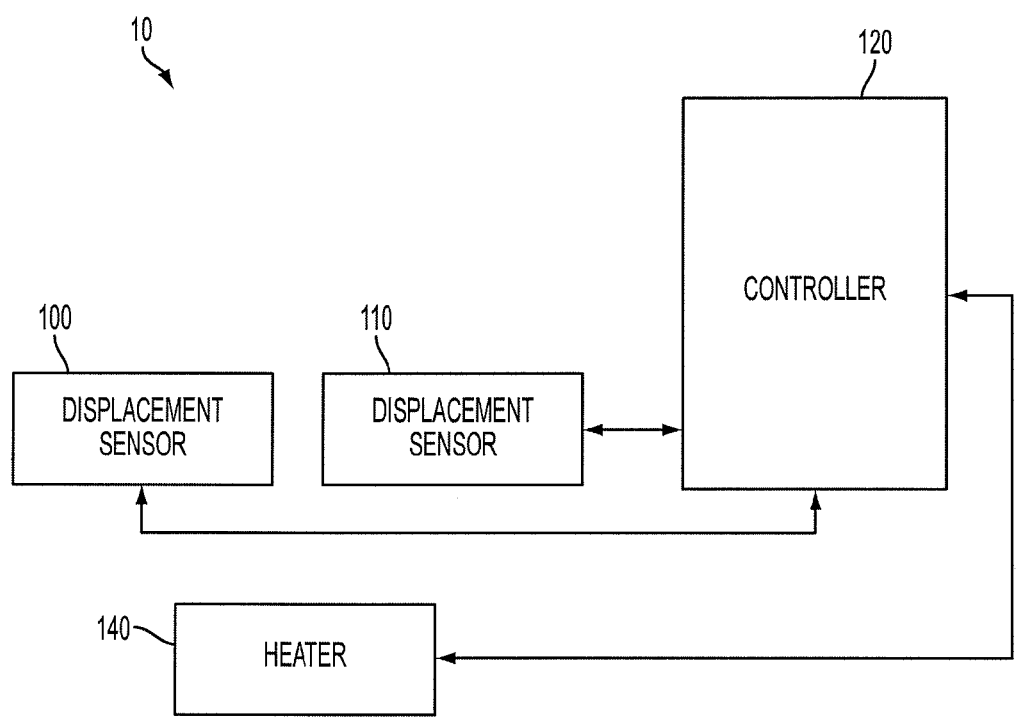
FIG. 1 shows a system for determining the thickness or change in thickness of a photovoltaic module.

In the following detailed description, reference is made to the accompanying drawings which form a part hereof, and in which is shown by way of illustration, specific embodiments that may be practiced. These embodiments are described in sufficient detail to enable those skilled in the art to make and use them, and it is to be understood that structural, logical, or procedural changes may be made to the specific embodiments disclosed without departing from the spirit and scope of the invention.

The methods and systems discussed herein can be used to complete thickness measurements faster than traditional methods, and can resolve small module thicknesses, including, for example, less than 1 micrometer. Further, use of such systems and techniques has demonstrated substantial improvement in accuracy.

In one aspect, a system for determining a thickness of a photovoltaic module can include a photovoltaic module support structure, configured so that a photovoltaic module received in the support structure is between the first and second displacement sensors. The system can include a controller in communication with the first and second displacement sensors. The controller can be configured to calculate a thickness of a photovoltaic module. The first and second displacement sensors can be positioned on a shared axis perpendicular to a plane where a photovoltaic module can be received such that the first and second displacement sensors are positioned on opposite sides of the plane. The first displacement sensor can be positioned on a first sensor axis and the second displacement sensor is positioned on a second sensor axis and the first and second sensor axes can be offset from each other and perpendicular to a plane where a photovoltaic module can be received such that the first and second displacement sensors can be positioned on opposite sides of the plane.

The system can include a heater proximate to the module support structure capable of heating a photovoltaic module. At least one of the first and second displacement sensors can include a contact displacement sensor. At least one of the first and second displacement sensors can include a non-contact displacement sensor. At least one of the first and second displacement sensors can include a light emitting sensing device, for example a laser emitter. The system can include one or more positioning devices configured to adjust the position of the first and second displacement sensors. One or more positioning devices can be in communication with the controller. The controller can be configured to adjust the position of the first and second displacement sensors via the one or more positioning devices.

The heater may be configured to heat a photovoltaic module received by the module support structure to about room temperature. The heater may be configured to heat a photovoltaic module received in the module support structure to a temperature other than room temperature, for example to more than about 70 degrees C., more than about 90 degrees C., less than about 120 degrees C., or less than about 100 degrees C. The controller may be configured to adjust the first and second displacement sensors simultaneously such that they maintain alignment on the shared axis, which moves relative to a photovoltaic module being measured while maintaining a perpendicular relationship to the plane between the sensors. The controller may be configured to calculate a change in thickness of a photovoltaic module. The controller may be configured to calculate a change in a thickness of a photovoltaic module in response to variance in temperature.

In another aspect, the system for determining a thickness of a photovoltaic module may include a support structure for the sensors that has a first arm and a second arm. The sensor support structure may be configured to receive the photovoltaic module between the first arm and the second arm. The system also includes a first sensor coupled to the first arm, and a second sensor coupled to the second arm, so that a photovoltaic module is received between the first and second sensors. The first and second sensors may be contact or non-contact sensors. The system may also include a controller coupled to the first and second sensors, wherein the controller receives data from the first and second sensors and calculates the thickness of the module using the received data. The controller may also communicate with servos to control the movement of the sensors. Additionally, the first sensor may be positioned to share with the second sensor an axis that is perpendicular to the planar surfaces of the received photovoltaic module.

A method for determining a thickness of a photovoltaic module can include positioning a photovoltaic module between first and second displacement sensors, such that the photovoltaic module defines a plane perpendicular to each of the first and second displacement sensors. A first measurement point of a first side of the photovoltaic module can correspond to the position of the first displacement sensor and a second measurement point of a second side of the photovoltaic module can correspond to the position of the second displacement sensor. The method can include calculating a first thickness of the photovoltaic module.

The first displacement sensor and second displacement sensor can be positioned on a shared axis and the first measurement point and second measurement point can be aligned on the shared axis. The method can include heating the photovoltaic module. The method can include calculating a second thickness of the photovoltaic module. Calculating the second thickness can include positioning the first displacement sensor at a third measurement point and positioning the second displacement sensor at a fourth measurement point.

Calculating a second thickness may include adjusting the position of the first and second displacement sensors or the position of the photovoltaic module, such that the shared axis intersects the photovoltaic module at different measurement points. Calculating a second thickness may include adjusting the first temperature of the photovoltaic module to a second temperature for thickness measurements at the same or different location on the photovoltaic module. The method may include comparing the calculated first and second thicknesses. The method may also include adjusting the first temperature to above about room temperature. The method may include adjusting the first temperature to above about 70 degrees C., above about 90 degrees C., below about 120 degrees C., or below about 100 degrees C.

In another aspect, the method may include positioning a first sensor next to the front side of the photovoltaic module, positioning a second sensor next to the back side of the photovoltaic module, the first and second sensors sharing an axis that is perpendicular to the front and back faces of the photovoltaic module, and calculating a first thickness for a first location on the photovoltaic module. The method may also include repositioning the sensors or the photovoltaic module with the first and second sensors maintaining the shared axis that is perpendicular to the front and back sides of the photovoltaic module, and calculating a second thickness for a second location on the photovoltaic module.

FIG. 1 shows a system 10 for determining a thickness or change in thickness of a photovoltaic module (which may be fully or partially encapsulated) that may include displacement sensors 100 and 110. System 10 may also include a controller 120 that may be coupled to the displacement sensors 100 and 110. Controller 120 may send commands to displacement sensors 100 and 110 and may receive data from the displacement sensors 100 and 110. The commands that may be sent to displacement sensors 100 and 110 may include commands to move, take measurements, initialize, power down, and other commands.

System 10 may also include a heater 140 that may be connected to and may receive commands from controller 120. Controller 120 may communicate with one or more components of system 10 using any suitable means, including, for example, any suitable form of hardwire or wireless communications.

System 10 may operate in a temperature-controlled environment. For example, heater 140 may raise or lower the temperature of the photovoltaic module, and thereby permit system 10 to measure the thickness of various areas of the photovoltaic module under various temperature conditions. Heater 140 can be connected to controller 120, which may be configured to adjust the temperature of photovoltaic module as desired. For example, controller 120 can be preprogrammed with a predetermined temperature scheme to monitor the thickness of the photovoltaic module under various temperature conditions. Controller 120 may be configured to determine how a change in temperature conditions effects a change in thickness of the photovoltaic module at one location or between different locations on the photovoltaic module.

Controller 120 may also be configured to control the conditions under which the thickness of the photovoltaic module is to be measured. For example, controller 120 may control the time, the temperature, and the frequency at which the photovoltaic module is measured. Controller 120 may also be configured to compare various calculated thicknesses to determine variance in thickness, as caused by any number of factors, including, for example, an increase or decrease in temperature. Controller 120 may include any suitable programmable means, including, for example, a microprocessor or computer to control one or more aspects of system 10.

Figure 2:
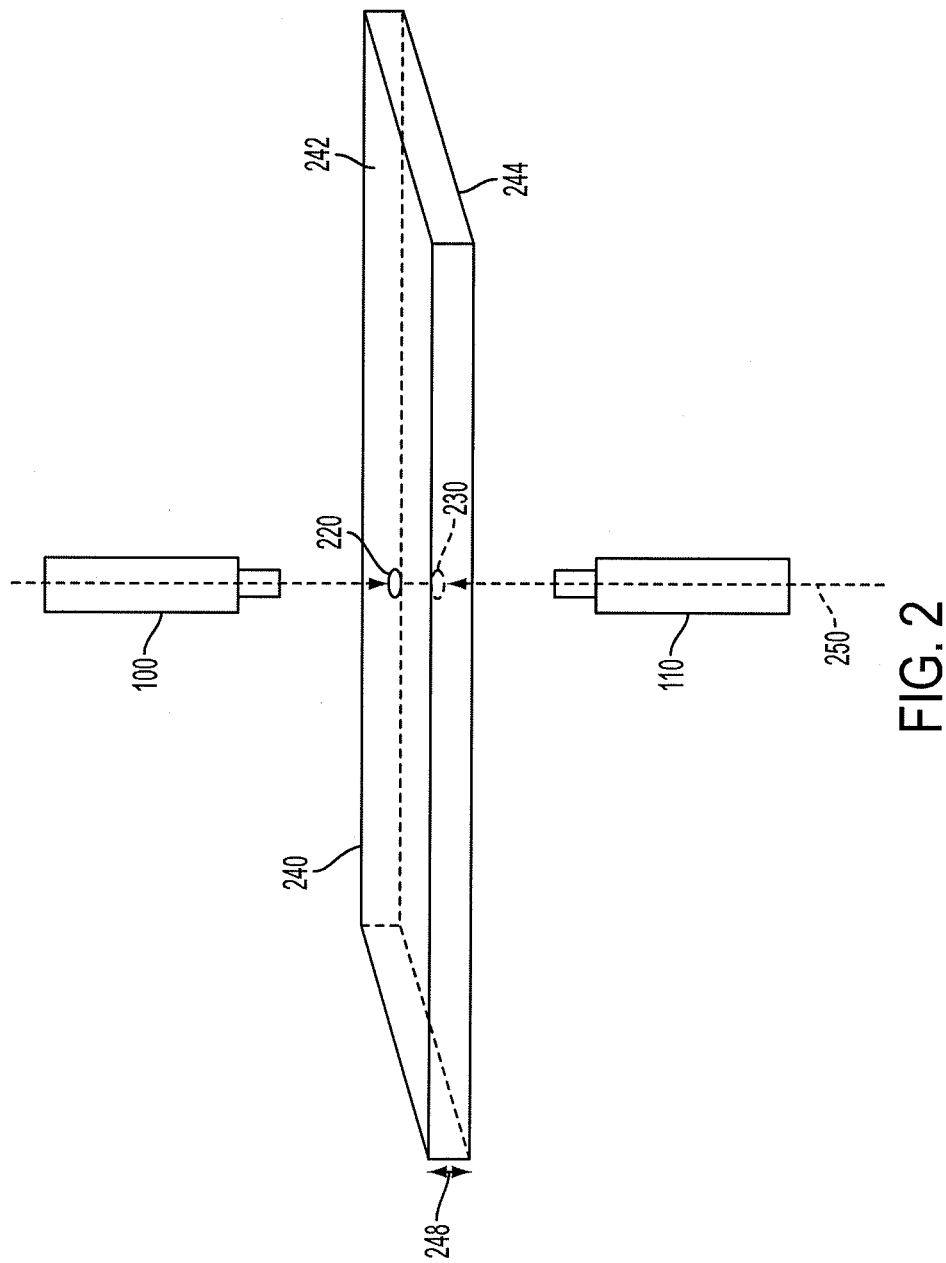
FIG. 2 shows two displacement sensors positioned proximate to a photovoltaic module.

FIG. 2 shows displacement sensors 100 and 110 which may include any suitable high resolution displacement sensor, including, for example, any suitable contact or non-contact displacement sensor. For example, displacement sensors 100 and 110 may include any suitable laser sensor or other light sensor. Displacement sensors 100 and 110 may be positioned on opposite sides of a photovoltaic module 240.

For example, displacement sensor 100 may be positioned adjacent to a front side 242 of photovoltaic module 240, and displacement sensor 110 may be positioned adjacent to a back side 244. Each displacement sensor 100 and 110 may be used to measure a distance between a reference location, such as the position of the sensor itself, and a location on photovoltaic module 240. Displacement sensor 100 may measure a distance between itself, as a reference location, and a first measurement point 220 on the photovoltaic module 240. Displacement sensor 110 may measure a distance between itself, as a reference location, and a second measurement point 230 on the photovoltaic module 240. The distances measured by the displacement sensors 100 and 110 may then be used to calculate a thickness 248 of photovoltaic module 240. For example, displacement sensor 100 may measure a distance of 10.2 mm between itself and photovoltaic module 240 and displacement sensor 110 may measure a distance of 10.5 mm between itself and photovoltaic module 240. If the distance between reference points for displacement sensors 100 and 110 is 27.5 mm, then thickness 248 of photovoltaic module 240 between first measurement point 220 and second measurement point 230 is equal to the distance between the displacement sensors 100 and 110 minus the distances between the displacement sensors 100 and 110 and photovoltaic module 240 or 6.8 mm.

If first measurement point 220 and second measurement point 230 are aligned so that they do not share an axis perpendicular to front side 242 and back side 244 of photovoltaic module 240, then the measured thickness may be greater than the actual thickness 248 of photovoltaic module 240. In some instances, it may be desirable to take measurements with axially offset sensors, but in most instances more accurate measurements are obtained when the sensors 100 and 110 are axially aligned.

To help reduce inaccuracies caused by misalignment, displacement sensors 100 and 110 may be positioned along a shared axis 250 that is perpendicular to the front and back sides 242 and 244 of photovoltaic module 240. By positioning the sensors 100 and 110 along the same axis, the corresponding points of measurement 220 and 230 on photovoltaic module 240 may be aligned.

Figure 3:
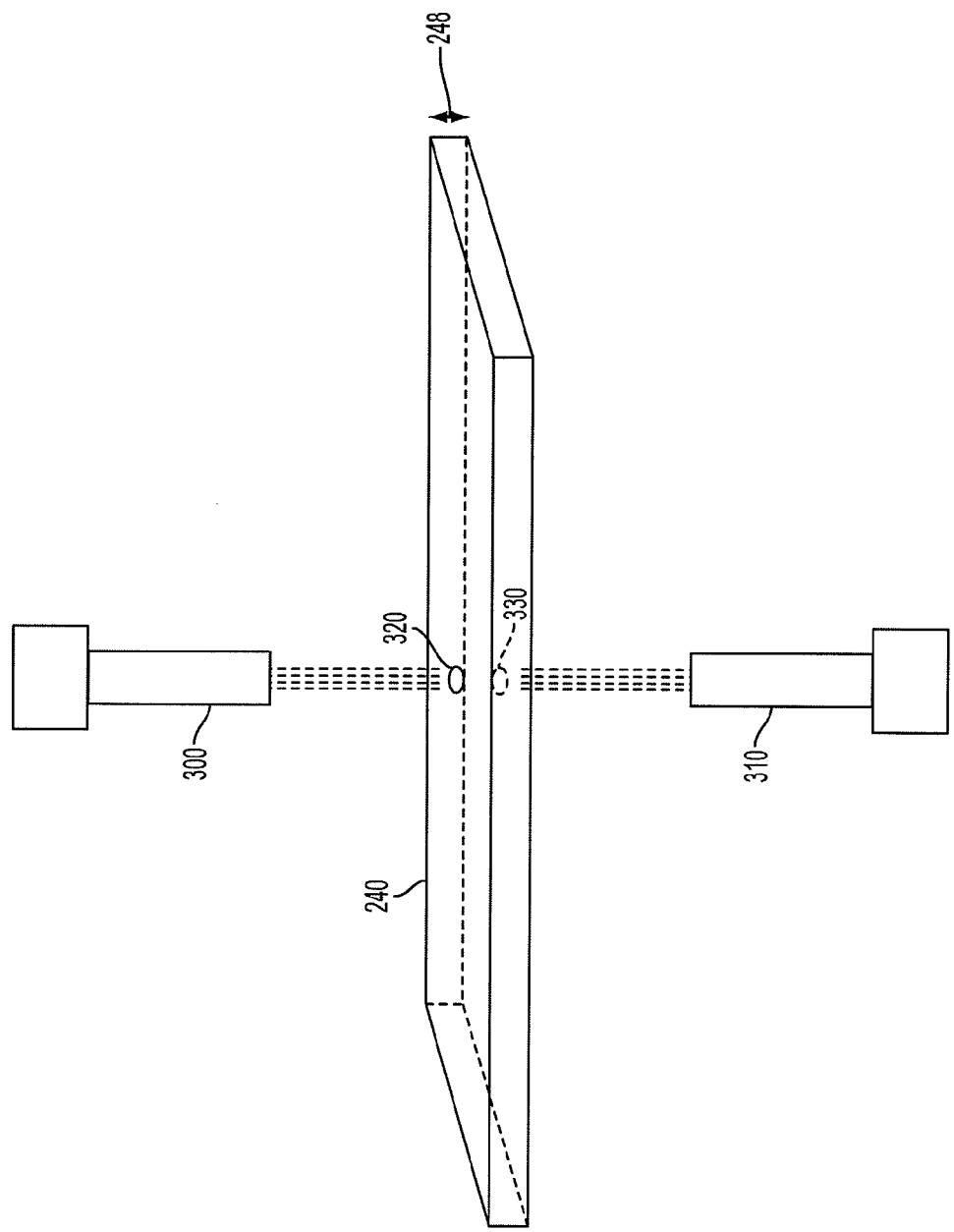
FIG. 3 shows two non-contact displacement sensors positioned proximate to a photovoltaic module.

Displacement sensors 100 and 110 may include any suitable non-contact sensors. For example, FIG. 3 shows non-contact displacement laser sensors 300 and 310, respectively, positioned proximate to photovoltaic module 240. The path of the laser of each laser sensor 300 and 310 may be aligned on the same axis, perpendicular with and passing through, photovoltaic module 240. Laser sensor 300 may operate to measure the distance between a known reference location, such as the laser sensor's 300 location and measurement point 320. Laser sensor 310 may operate to measure the distance between a known reference location, such as the laser sensor's 310 location and measurement point 330. The distances measured by the laser sensors 310 and 320 may be used to calculate thickness 248 of module 240.

Figure 4:
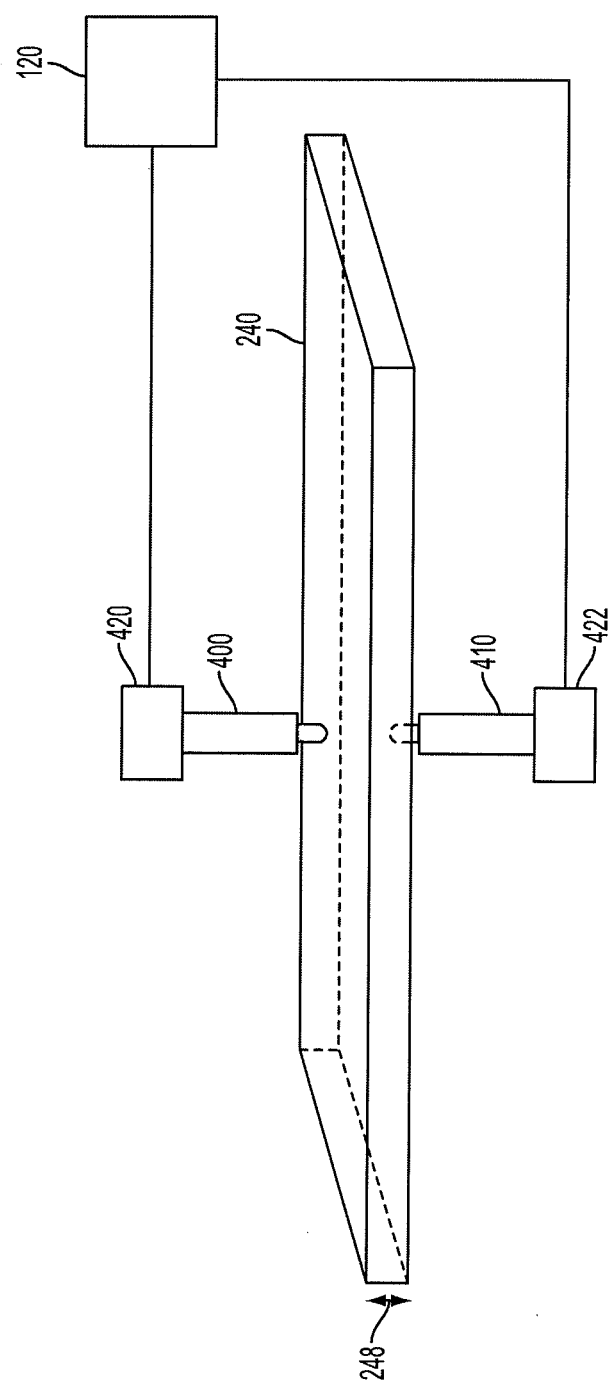
FIG. 4 shows two contact displacement sensors positioned proximate to a photovoltaic module.

Displacement sensors 100 and 110 may also include any suitable contact sensors. For example, FIG. 4 shows contact displacement sensors 400 and 410, respectively, positioned proximate to photovoltaic module 240. Contact sensors 400 and 410 may move from known locations, such as their starting locations, into contact with photovoltaic module 240. The distance each contact sensor 400 and 410 moves from a separate reference point may be measured and used to calculate thickness 248 of photovoltaic module 240.

Contact sensor 400 may be connected to servo 420. Servo 420 may be used to move contact sensor 400 into contact with photovoltaic module 240. Servo 420 may contain a motor and a load sensor. Servo 420 may use the load sensor to detect changes in current in the motor to determine when contact sensor 400 contacts photovoltaic module 240. For example, as servo 420 moves contact sensors 400 into contact with photovoltaic module 240 the current in the motor may maintain steady. However, once contact sensor 400 contacts photovoltaic module 240, the load on the motor may increase thereby increasing the current in the motor. The load sensor may detect the increase in current and stop the movement of servo 420 and thereby stop contact sensor 400. Servo 420 may measure the distance the contact sensor 400 moved to contact photovoltaic module 240.

Contact sensor 410 may be connected to servo 422. Servo 422 may be used to move contact sensor 410 into contact with photovoltaic module 240. Servo 422 may function similar to servo 420 and may measure the distance the contact sensor 410 moved from a reference position to contact photovoltaic module 240. If one of the contact sensors 400 and 410 contacts photovoltaic module 240 before the other, photovoltaic module 240 may move slightly because of the contact. However, once the other of the contact sensors 400 and 410 contacts photovoltaic module 240, photovoltaic module 240 may return to its original location.

Servos 420 and 422 may both be in communication with controller 120. Servos 420 and 422 may be connected directly, wirelessly, or through a network to controller 120. Servos 420 and 422 may receive instructions from and send measurement data to controller 120. Measurements taken by servos 420 and 422 may be inaccurate if they are taken before both contact sensors 400 and 410 are in contact with photovoltaic module 240. As a result, controller 120 may operate servos 420 and 422 to take and send measurements to controller 120 after both contact sensors 400 and 410 contact photovoltaic module 240.

Figure 5:
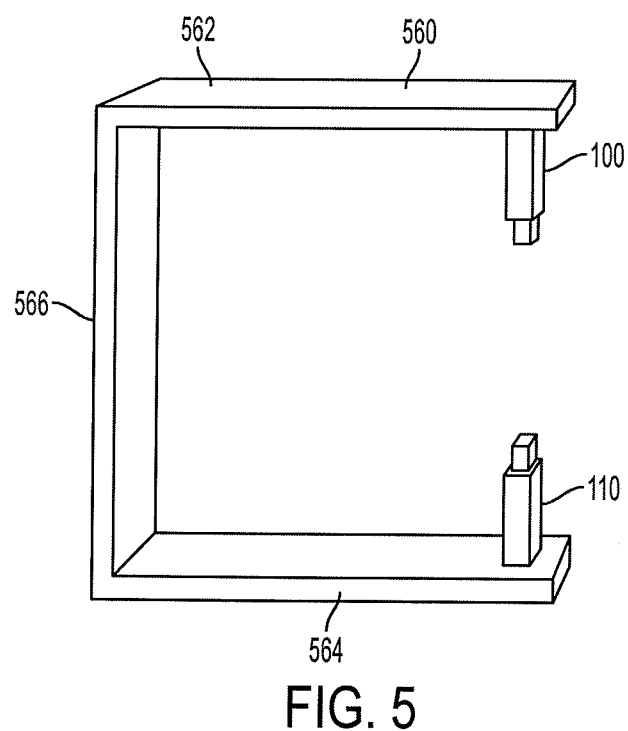
FIG. 5 shows a sensor support structure for supporting the two displacement sensors.

Displacement sensors 100 and 110 may be physically connected to maintain their positions relative to each other despite temperature fluctuations or the movement of one of the displacement sensors 100 and 110. Displacement sensors 100 and 110 may be physically connected by any suitable structure, including, for example, a sensor support structure 560 as shown in FIG. 5. Sensor support structure 560 may include a first arm 562 and a second arm 564 connected by a cross arm 566. First displacement sensor 100 may be connected to first arm 562. Second displacement sensor 110 may be connected to second arm 564. Sensor support structure 560 may be formed by any suitable material or combination of materials, including a metal such as aluminum.

Figure 6:
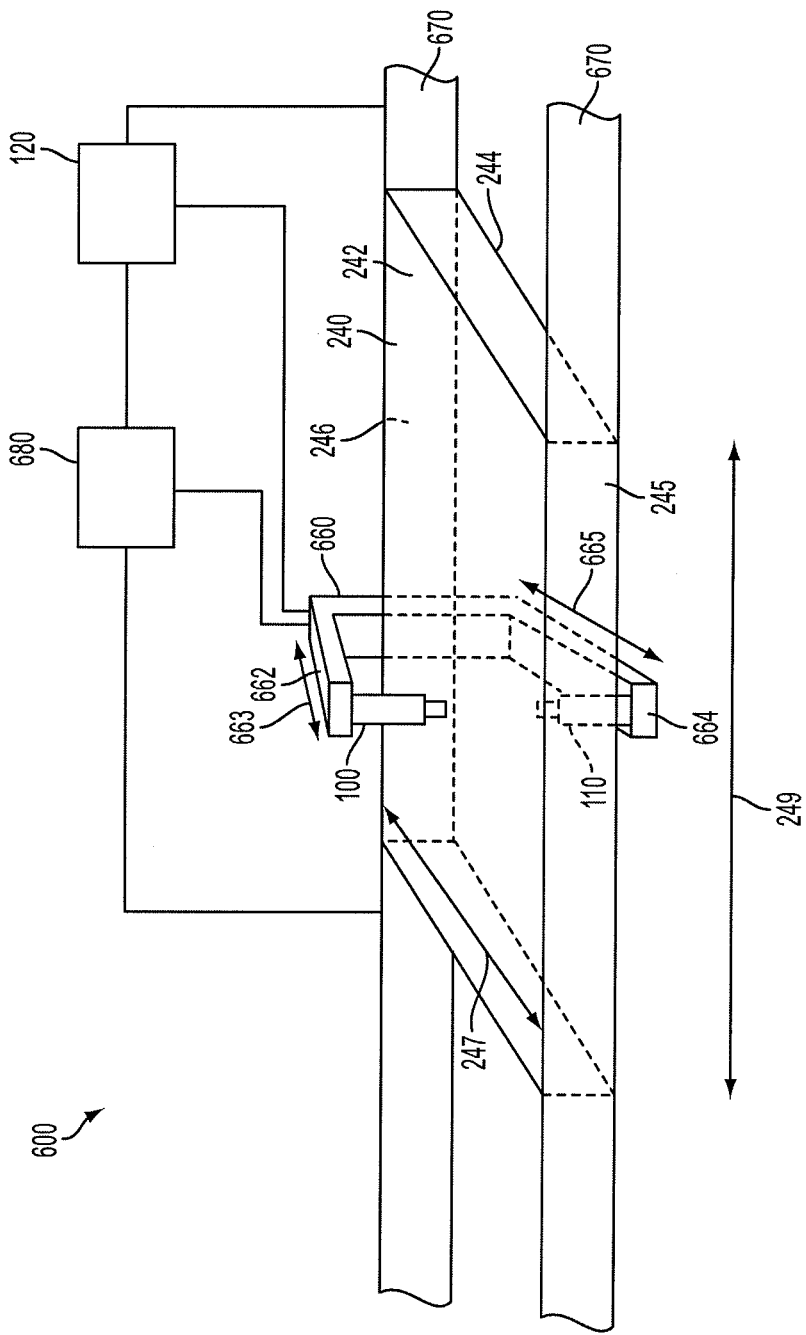
FIG. 6 shows a measurement system for supporting two displacement sensors positioned proximate to a photovoltaic module.

FIG. 6 shows a measurement system 600 that may support displacement sensors 100 and 110 and a photovoltaic module 240 and may be used to measure thickness 248 of photovoltaic module 240. Measurement system 600 includes a pair of spaced tracks 670 in which the sides 245 and 246 of photovoltaic module 240 may travel. Photovoltaic module 240 may be coupled to tracks 670 so that photovoltaic module 240 may move along tracks 670. Tracks 670 may be part of a production line assembly and thickness 248 of photovoltaic module 240 may be measured at selected measuring points on the module 240 as photovoltaic module 240 moves along tracks 670 or a photovoltaic module 240 may move along the tracks 670 to a measuring position where it temporarily stops for measurements to be taken. Movement mechanism 680 may move photovoltaic module 240 along tracks 670. Alternatively, tracks 670 may be replaced by respective rails or belts which support side edges of a photovoltaic module, allowing the surface areas of the front side 242 and back side 244 of the module to be accessed by the sensors 100, 110.

Measurement system 600 may also include a sensor support structure 660 that may connect and support displacement sensors 100 and 110. Sensor support structure 660 may have a first arm 662 and a second arm 664 that have lengths 663 and 665, respectively, that are equal to or greater than a width 247 of photovoltaic module 240. First and second arms 662 and 664 may be designed to receive photovoltaic module 240 there between.

Displacement sensor 100 may be coupled to first arm 662 and displacement sensor 110 may be coupled to second arm 664. Displacement sensors 100 and 110 may be positioned along first and second arms 662 and 664 so that displacement sensor 100 shares with displacement sensor 110 an axis that is perpendicular to the front and back sides 242 and 244 of photovoltaic module 240. Movement mechanism 680 may move sensor support structure 660 to enable displacement sensors 100 and 110 to be located at any position along the entire width 247 of photovoltaic module 240. Movement mechanism 680 may move sensor support structure 660 using worm gears, other gears, actuators, servos, or other known mechanisms.

In another embodiment, displacement sensors 100 and 110 may be movably coupled to first and second arms 662 and 664, respectively. In this embodiment, movement mechanism 680 may move displacement sensors 100 and 110 along first and second arms 662 and 664 to any position along width 247 of photovoltaic module 240. Movement mechanism 680 may move displacement sensors 100 and 110 independently along first and second arms 662 and 664 or may be coupled and move together. Movement mechanism 680 may move displacement sensors 100 and 110 using worm gears, other gears, actuators, servos, or other known mechanisms.

Movement mechanism 680 may move photovoltaic module 240 along tracks 670 to enable displacement sensors 100 and 110 to be positioned along the entire length 249 of photovoltaic module 240. Alternatively, movement mechanism 680 may move sensor support structure 660 along length 249 of photovoltaic module 240 so that displacement sensors 100 and 110 may be positioned along the entire length 249 of photovoltaic module 240.

Movement mechanism 680 may be connected to controller 120, directly, wireless, or through a network. Controller 120 may control the position of sensor support structure 660 along the width and length of photovoltaic module 240 using movement mechanism 680. Controller 120 may also control the position of displacement sensors 100 and 110 along first and second arms 662 and 664 using movement mechanism 680. Controller 120 may control the movement and position of displacement sensors 100 and 110 so that displacement sensors 100 and 110 maintain the shared axis that is perpendicular to the front panel of the received photovoltaic module. Controller 120 may also control a mechanism for moving the photovoltaic module 240 to control the position of photovoltaic module 240 along tracks 670 or may control movement of the tracks 670 themselves to move a photovoltaic module 240. Controller 120 may thereby position displacement sensors 100 and 110 to measure thickness 248 of all areas of photovoltaic module 240. Controller 120 may also be configured to move displacement sensors 100 and 110 to measure the change or difference in thickness 248 between regions of photovoltaic module 240. Before a thickness measurement is taken, displacement sensors 100 and 110 may be calibrated via an NIST (National Institute of Standards Technology) traceable thickness gauge to identify the validity of the measurement of photovoltaic module 240.

Figure 7:
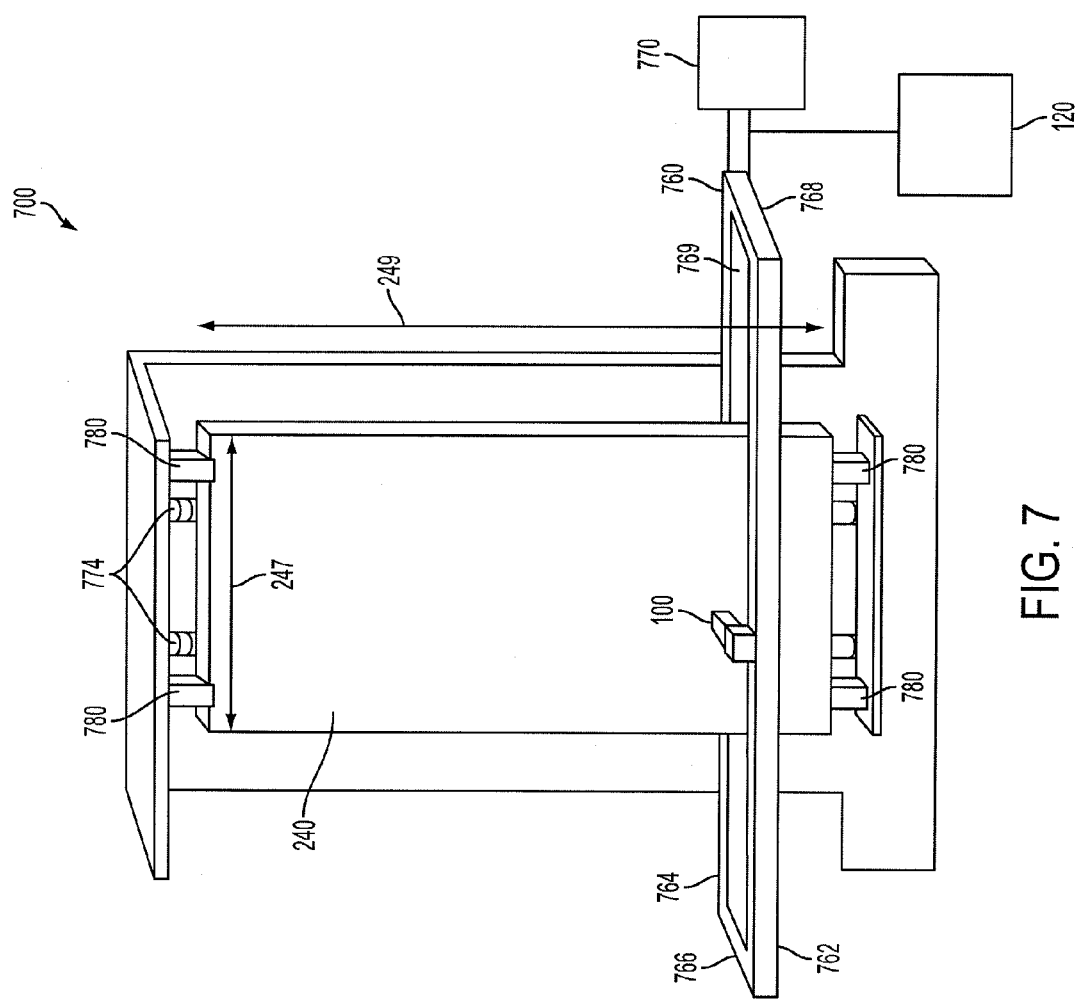
FIG. 7 shows a measurement system for supporting two displacement sensors positioned proximate to a photovoltaic module.

FIG. 7 shows another embodiment of a measurement system 700 that may support displacement sensors 100 and 110 and photovoltaic module 240. Measurement system 700 includes a sensor support receptacle 760 and a photovoltaic module support structure 780. Photovoltaic module support structure 780 supports and receives photovoltaic module 240. Sensor support receptacle 760 includes a first arm 762, a second arm 764, a first end 766, and a second end 768. First arm 762, second arm 764, first end 765, and second end 768 form a rectangle with an opening 769 of sufficient dimensions to allow receptacle 760 to move relative to a photovoltaic module 240 which receptacle 760 surrounds. First arm 762 may be coupled to displacement sensor 100 and second arm 764 may be coupled to displacement sensor 110. Displacement sensors 100 and 110 may be positioned along first and second arms 762 and 764 so that displacement sensor 100 shares with displacement sensor 110 an axis that is perpendicular to the front and back sides 242 and 244 of photovoltaic module 240 when photovoltaic module 240 is placed in opening 769.

Opening 769 may be of sufficient dimensions so that receptacle 760 may move to locate displacement sensors 100 and 110 along the entire width 247 of photovoltaic module 240. Receptacle 760 may also move along linear runners 774 to locate displacement sensors 100 and 110 along the entire length 249 of photovoltaic module 240. Movement mechanism 770 may move receptacle 760 using worm gears, other gears, actuators, servos, or other known mechanisms. Alternatively, movement mechanism 770 may move displacement sensors 100 and 110 along first and second arms 762 and 764 to any position along width 247 of photovoltaic module 240. Displacement sensors 100 and 110 may move independently along the first and second arms 762 and 764 or may be coupled and move together. Movement mechanism 770 may move displacement sensors 100 and 110 using worm gears, other gears, actuators, servos, or other known mechanisms.

Movement mechanism 770 may be connected to controller 120, directly, wireless, or through a network. Controller 120 may control the position of receptacle 760 using movement mechanism 770. Controller 120 may also control the position of displacement sensors 100 and 110 using movement mechanism 770. Controller 120 may control the position of displacement sensors 100 and 110 so that displacement sensors 100 and 110 maintain the shared axis that is perpendicular to the front panel of the received photovoltaic module when they are moved. Controller 120 may thereby move and position displacement sensors 100 and 110 to measure thickness 248 of all areas of photovoltaic module 240. Controller 120 may also be configured to move displacement sensors 100 and 110 to measure the change or difference in thickness 248 between regions of photovoltaic module 240.

While embodiments have been described in detail, it should be readily understood that the invention is not limited to the disclosed embodiments. Rather the embodiments can be modified to incorporate any number of variations, alterations, substitutions or equivalent arrangements not heretofore described. Although certain features have been described with some embodiments of the carrier, such features can be employed in other disclosed embodiments of the carrier as well. Accordingly, the invention is not limited by the foregoing embodiments, but is only limited by the scope of the appended claims

What is claimed as new and desired to be protected by Letters Patent of the United States is:

1. A system for identifying whether a photovoltaic module is pinched, the system comprising:
   a photovoltaic module support structure; a first displacement sensor and a second displacement sensor positioned proximate the support structure so that a photovoltaic module received in the support structure is between the first and second displacement sensors;
   a heater proximate to the support structure capable of heating a photovoltaic module located in the support structure; and,
   a controller in communication with the first and second displacement sensors, and configured to calculate a thickness of a photovoltaic module received by the support structure and determine if the photovoltaic module is pinched.

2. The system of claim 1, wherein the first and second displacement sensors are positioned on a shared axis perpendicular to a surface of a photovoltaic module when the module is received in the support structure such that the first and second displacement sensors are positioned on opposite sides of the module.

3. The system of claim 2, wherein the controller is configured to adjust the first and second displacement sensors simultaneously such that they maintain alignment on the shared axis, which moves while maintaining a perpendicular relationship to a module that is received in the support structure.

4. The system of claim 1, wherein the first displacement sensor is positioned on a first sensor axis and the second displacement sensor is positioned on a second sensor axis and the first and second sensor axes are offset from each other and perpendicular to a photovoltaic module when received in the support structure such that the first and second displacement sensors are positioned on opposite sides of the module.

5. The system of claim 1, wherein the support structure comprises a track for supporting the photovoltaic module.

6. The system of claim 5, further comprising a mechanism for moving a photovoltaic module along the track.

7. The system of claim 6, wherein the track is part of a production line.

8. The system of claim 1, further comprising a receptacle that supports the sensors.

9. The system of claim 8, wherein the receptacle surrounds a photovoltaic module received in the support structure.

10. A system for determining a thickness of a photovoltaic module, the system comprising:
a photovoltaic module support structure; a first displacement sensor and a second displacement sensor positioned proximate the support structure so that a photovoltaic module received in the support structure is between the first and second displacement sensors;
a controller in communication with the first and second displacement sensors, and configured to calculate a thickness of a photovoltaic module received by the support structure; and, a heater proximate to the support structure capable of heating a photovoltaic module located in the support structure.

11. The system of claim 10, wherein the heater is configured to heat a photovoltaic module received in the support structure to about room temperature.

12. The system of claim 10, wherein the heater is configured to heat a photovoltaic module received in the support structure to more than about 70 degrees C.

13. The system of claim 10, wherein the heater is configured to heat a photovoltaic module received in the support structure to more than about 90 degrees C.

14. The system of claim 10, wherein the heater is configured to heat a photovoltaic module received in the support structure to less than about 120 degrees C.

15. The system of claim 10, wherein the heater is configured to heat a photovoltaic module received in the support structure to less than about 100 degrees C.

16. The system of claim 10, wherein the controller is configured to calculate a change in thickness of a photovoltaic module secured by said support structure in response to variance in temperature.

17. The system of claim 1, wherein at least one of the first and second displacement sensors comprises a contact displacement sensor.

18. The system of claim 1, wherein at least one of the first and second displacement sensors comprises a non-contact displacement sensor.

19. The system of claim 18, wherein the non-contact displacement sensor uses light.

20. The system of claim 19, wherein the non-contact displacement sensor is a laser sensor.

21. The system of claim 1, further comprising a mechanism for providing relative movement between the first and second displacement sensors and a length of a photovoltaic module secured by said support structure.

22. The system of claim 1, further comprising a mechanism for providing relative movement between the first and second displacement sensors and a width of a photovoltaic module secured by said support structure.

23. The system of claim 1, further comprising one or more positioning devices configured to adjust the first and second displacement sensors.

24. The system of claim 23, wherein the one or more positioning devices are in communication with the controller.

25. The system of claim 24, wherein the controller is further configured to adjust the first and second displacement sensors via the one or more positioning devices.

26. The system of claim 1, wherein the first and second displacement sensors measure a distance from each respective sensor to a photovoltaic module secured by said support structure.

27. The system of claim 26, wherein the controller uses the measured distances to calculate the thickness of a photovoltaic module secured by said support structure.

28. The system of claim 1, wherein the controller is configured to calculate a change in thickness of a photovoltaic module received by the support structure.

29. A method for identifying whether a photovoltaic module is pinched, the method comprising:
positioning a first sensor next to the front side of the photovoltaic module; positioning a second sensor next to the back side of the photovoltaic module, the first and second sensors sharing an axis that is perpendicular to the front and back sides of the photovoltaic module;
heating the photovoltaic module;
calculating a first thickness at a first location of the heated photovoltaic module and calculating a second thickness at a second location of the heated photovoltaic module which is different from the first location; and,
determining if the photovoltaic module is pinched from the calculated thicknesses.

30. The method of claim 29, wherein calculating a second thickness includes:
repositioning the first sensor along the front side of the photovoltaic module;
repositioning the second sensor along the back side of the photovoltaic module, the first and second sensors maintaining the shared axis that is perpendicular to the front and back sides of the photovoltaic module; and
calculating a second thickness at a second location of the photovoltaic module.

31. The method of claim 30, further comprising comparing the calculated first and second thicknesses.

32. A method for determining a thickness between a front side and a back side of a photovoltaic module, the method comprising:
positioning a first sensor next to the front side of the photovoltaic module; positioning a second sensor next to the back side of the photovoltaic module, the first and second sensors sharing an axis that is perpendicular to the front and back sides of the photovoltaic module;
calculating a first thickness at a first location of the photovoltaic module using said sensors;
repositioning the first sensor along the front side of the photovoltaic module;
repositioning the second sensor along the back side of the photovoltaic module, the first and second sensors maintaining the shared axis that is perpendicular to the front and back sides of the photovoltaic module;
calculating a second thickness at a second location of the photovoltaic module; and
heating the photovoltaic module.

33. The method of claim 32, further comprising
calculating the second thickness after heating the photovoltaic module;
calculating the first thickness after heating the photovoltaic module; and
comparing the calculated first and second thickness obtained after heating the photovoltaic module.

34. The method of claim 32, further comprising using said heater to adjust a first temperature of the photovoltaic module to above about room temperature.

35. The method of claim 32, further comprising using said heater to adjust a first temperature of the photovoltaic module to above about 70 degrees C.

36. The method of claim 32, further comprising using said heater to adjust a first temperature of the photovoltaic module to above about 90 degrees C.

37. The method of claim 32, further comprising using said heater to adjust a first temperature of the photovoltaic module to below about 120 degrees C.

38. The method of claim 32, further comprising using said heater to adjust a first temperature of the photovoltaic module to below about 100 degrees C.

39. The method of claim 30, wherein the first and second sensors are coupled to a common sensor support structure.

40. The method of claim 39, wherein the steps of repositioning the first and second sensors are accomplished by moving the common sensor support structure.

41. The method of claim 29, wherein the first and second sensors are coupled to a common sensor support structure.

42. The method of claim 41, wherein the steps of positioning the first and second sensors are accomplished by moving the common sensor support structure.

43. The method of claim 29, wherein the first and second sensors are non-contact sensors.

44. The method of claim 29, wherein the first and second sensors are contact sensors.

* * * * *